United States Patent [19]

Haehn

[11] Patent Number: 5,336,838

[45] Date of Patent: Aug. 9, 1994

[54] ABSORPTION COLUMN WITH INTERNAL MIXING CHAMBER FOR ABSORPTION OF ACETYLENE

[75] Inventor: Peter-Clemens Haehn, Geretsried, Fed. Rep. of Germany

[73] Assignee: Linde Aktiengesellschaft, Wiesbaden, Fed. Rep. of Germany

[21] Appl. No.: 980,868

[22] Filed: Nov. 24, 1992

Related U.S. Application Data

[63] Continuation of Ser. No. 933,590, Aug. 24, 1992, abandoned.

[30] Foreign Application Priority Data

Aug. 23, 1991 [DE] Fed. Rep. of Germany ....... 4127988

[51] Int. Cl.$^5$ ............................ C07C 7/10; B01D 19/00
[52] U.S. Cl. ..................................... 585/833; 95/155
[58] Field of Search ...................... 585/833; 55/63, 64

[56] References Cited

U.S. PATENT DOCUMENTS 4,655,798 4/1987 Ruch et al. ............................ 55/64

Primary Examiner—Anthony McFarlane
Assistant Examiner—Nhat D. Phan
Attorney, Agent, or Firm—Millen, White, Zelano, & Branigan

[57] ABSTRACT

In the absorption of acetylene from a crude gas mixture containing mostly $C_2$ hydrocarbons, a substantially acetylene-free liquid $C_2$ stream is introduced into a mixing chamber located in the column between the feed points for the crude gas mixture and the absorption agent. The $C_2$ stream is distributed into fine droplets as it enters into accumulated absorption agent in the mixing chamber, so that foam is not formed in the absorption column. The mixing chamber can be formed of a mixing tank integrated with a plate.

11 Claims, 1 Drawing Sheet

ABSORPTION COLUMN WITH INTERNAL MIXING CHAMBER FOR ABSORPTION OF ACETYLENE

CROSS-REFERENCE TO RELATED APPLICATION

This application is a continuation of Application Ser. No. 07/933,590, filed Aug. 24, 1992, now abandoned; and is related to a concurrently filed application, "Absorption Columns with External Mixing for Absorption of Acetylene", claiming priority of German Application P 41 27 987.5, filed Aug. 23, 1991.

BACKGROUND OF THE INVENTION

This invention relates to a gas absorption process and apparatus, particularly for scrubbing acetylene out of a crude gas mixture containing mostly $C_2$ hydrocarbons.

The invention is especially directed to an improvement in the operation of a plate column, wherein the crude gas mixture is fed into the lower zone of the absorption column; fresh or regenerated absorption agent is fed to the upper zone of the absorption column; loaded absorption agent is drawn off the bottom of the absorption column and is fed to a regeneration stage; a substantially acetylene-free product gas stream is withdrawn from the head of the absorption column, optionally after separation and recycling of a reflux condensate to the absorption column, and wherein a substantially acetylene-free liquid $C_2$ stream is introduced into the absorption column between the respective feed points for the crude gas mixture and the absorption agent.

In the extraction of ethylene from a thermally cracked cut of hydrocarbons, a crude gas mixture is obtained containing mostly $C_2$ hydrocarbons (ethylene, acetylene and optionally ethane). Besides the $C_2$ hydrocarbons, the crude gas mixture may also contain $C_3$ hydrocarbons and/or methane. Acetylene is generally removed from the crude gas mixture by scrubbing with an absorption agent selective for acetylene. In this connection, EP-B 0 158 280, corresponding to U.S. Pat. No. 4,655,798, teaches a process comprising passing an additional feed of a substantially acetylene-free, liquid, $C_2$ stream into the absorption column. Despite the introduction of this acetylene-free $C_2$ stream, foam is formed time and again in the absorption column, and this foam is highly undesirable since it results in downtime and/or the escape acetylene into the product gas. The formation of both hydrocarbon-rich and hydrocarbon-poor liquid phases, in addition to the vapor phase, are generally responsible for the foam. These two liquid phases are formed when the saturation limit of the absorption agent is exceeded relative to the hydrocarbons present. But foam formation can also occur far below the saturation limit in the absorption column, particularly under unstable operating conditions.

SUMMARY OF THE INVENTION

An object of this invention, therefore, is to provide a process and apparatus in which foam is largely or completely prevented.

Upon further study of the specification and appended claims, further objects and advantages of this invention will become apparent to those skilled in the art.

These objects are achieved according to the invention by introducing fine droplets of the substantially acetylene-free liquid, $C_2$ stream into a pool of absorption agent accumulating in the column. By virtue of the method of introducing the substantially acetylene-free $C_2$ stream into the absorption agent, the $C_2$ stream and this absorption agent are mixed without causing the formation of foam.

This prevention of the foaming of the absorption agent is quite unexpected, and it occurs even if the absorption agent is almost completely saturated with hydrocarbons.

For the process according to the invention, all absorption agents are suitable which exhibit a selective solubilizing power for acetylene as compared to ethylene, such as, for example, N-methylpyrrolidone (NMP) or dimethylformamide (DMF).

The crude gas mixture containing mostly $C_2$ hydrocarbon generally contains on a percent by volume basis about 0.5 to about 4.0 acetylene and about 95.0 to about 99.0 other $C_2$ hydrocarbons.

The substantially acetylene-free liquid $C_2$ stream generally contains in percent by weight basis, less than about 5 ppm, especially less than about 0.5 ppm, acetylene.

The temperature and pressure conditions in the column are generally about 210 to 283, preferably 238 to 273° K and about 6.0 to 30.0, preferably 15.0 to 30.0 bar.

The pressure of the substantially acetylene-free liquid $C_2$ stream entering the column must be higher than the pressure of the column at the location of $C_2$ feed point.

Special advantages in the process according to the invention can be produced if the absorption agent is accumulated in a mixing zone which is integrated with a tray (plate) of the absorption column. Into this mixing zone are fed the absorption agent from the plate above and the substantially acetylene-free liquid $C_2$ stream. In this way, the $C_2$ stream is especially well mixed with the absorption agent accumulated in the mixing zone.

As a particular embodiment of the invention, the absorption agent can be introduced from the plate above by an immersion tube in the mixing zone. Also, it is preferred to introduce the substantially acetylene-free liquid $C_2$ stream into the mixing zone at a location below the introduction of the absorption agent, which also increases the efficiency of the mixing step.

In a still further modification of the invention, the substantially acetylene-free $C_2$ stream is preferably introduced at a temperature which is below the temperature of the absorption agent in which said $C_2$ stream is mixed. This serves to cool the absorption agent, thereby increasing the solubilizing power of the absorption agent relative to acetylene. For example, it is preferred that temperature of the $C_2$ stream is about 1° to 20°, preferably 2° to 15° below the temperature of the absorption agent.

The $C_2$ stream is advantageously introduced into the lower two thirds, preferably in the lower half of the absorption column. In further preferred aspect of the invention, several substantially acetylene-free liquid $C_2$ streams can be fed into the absorption column on several trays. In this way, by introducing several $C_2$ streams with different temperatures, a desired temperature profile can be adjusted in the absorption column.

With additional advantage, the mixing zone can be filled with any type of packing, e.g., structured packing, Raschig rings, etc. In this way, not only is the mixing of the $C_2$ stream and absorption agent improved, but also the gas liquid contact is more efficient.

In the apparatus aspect of this invention, there is provided an absorption column having several plates, a feed pipe for the crude gas mixture, a feed pipe for fresh and/or regenerated absorbing agent, a feed pipe for the substantially acetylene-free liquid $C_2$ stream, an outlet for the acetylene-free product gas stream, and an outlet for the loaded absorption agent. In addition, the apparatus comprises a mixing tank, open on top, installed in a plate, an immersion tube projecting from an upper plate downwardly into the mixing tank, permitting the absorption agent on an upper plate to fall into the mixing tank, and a feed pipe for the substantially acetylene-free liquid $C_2$ stream installed through the wall of the absorption column and leading into the mixing tank.

The feed pipe for the substantially acetylene-free liquid $C_2$ stream is preferably branched into several outlet pipes in the mixing tank, so as to permit thorough mixing in the mixing tank. In an especially advantageous embodiment, the outlet pipes are furnished with multiple orifices as outlet openings in the nature of a spray head or distributor so that finely divided $C_2$ stream can be passed into the absorbing agent.

As a further modification of the apparatus, multiple feed pipes for accommodating multiple acetylene-free liquid $C_2$ streams are provided at several plate locations in the absorption column. The absorption column in this case contains several plates, each provided with a feed pipe for the substantially acetylene-free liquid $C_2$ stream into a respective mixing tank on each plate.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
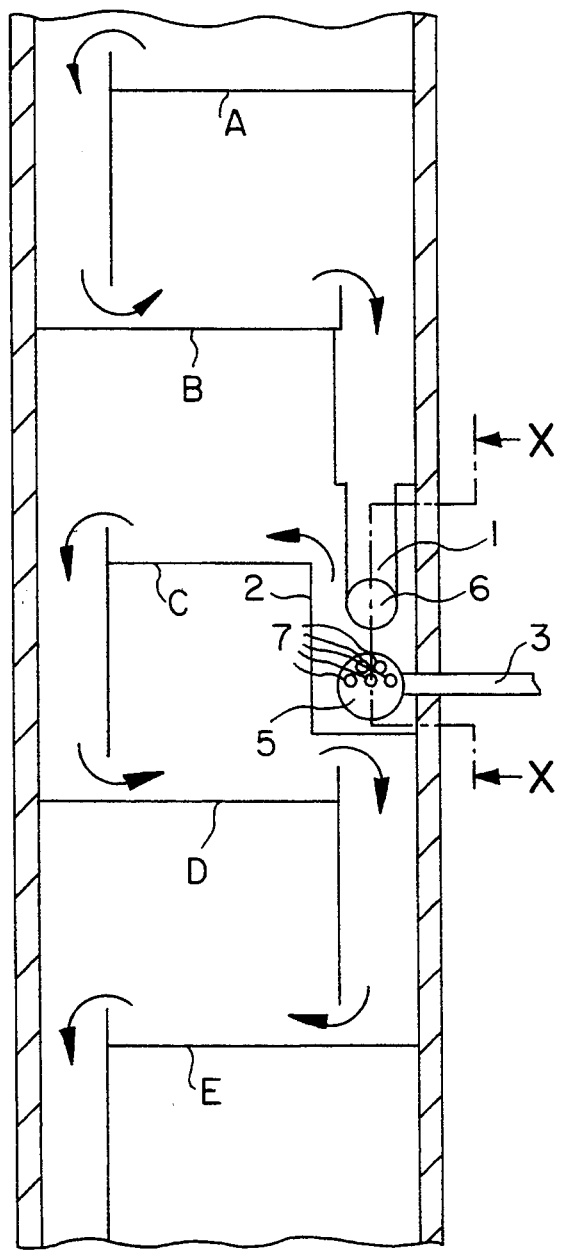
FIG. 1 is a cutaway front vertical schematic section of an absorption column according to the invention.

FIG. 1 shows a cutaway portion of an absorption column wherein plates A, B, C, D and E are, for example, bubble plates or sieve plates, each respectively provided with an offset downcomer in the absorption column. The absorption agent falls countercurrent to the rising gas from one plate to the plate lying underneath via a plate downcomer. The direction of the absorption agent flowing downwardly in the absorption column is represented by arrows.

The downcomer of plate B leads into immersion tube 1 which projects into mixing tank 2, provided in plate C. Feed pipe 3 for the substantially acetylene-free liquid $C_2$ stream ends in mixing tank 2 in a cross pipe 4, which is closed with pipe end pieces 5. The absorption agent flows via immersion tube 1 and T-fitting conduit 6 into the mixing tank 2. The substantially acetylene-free liquid $C_2$, stream is introduced into the mixing tank 2 via pipe 3, cross pipe 4 and outlet openings 7 in cross pipe 4 and in end piece 5. The substantially acetylene-free liquid $C_2$ stream is evaporated and mixed with the absorption agent accumulated in the mixing zone, i.e., in mixing tank 2. The design of the mixing tank 2 is made taking into consideration the degassing times for the evaporating $C_2$ stream.

Utilizing the $C_2$ stream, colder than the absorption agent, the absorption agent in mixing tank 2 is additionally undercooled. The absorption agent then passes into plate C and according to the arrows, to plate D, E, etc.

Figure 2:
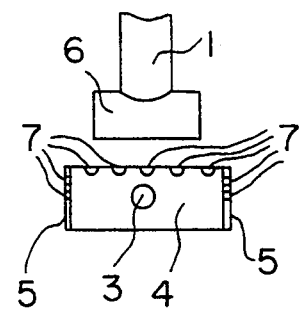
FIG. 2 is a schematic end view of the feed pipe, immersion tube and distributor.

In FIG. 2, immersion tube 1 is illustrated with a cross pipe 6, as well as feed pipe 3 for the $C_2$ stream, cross pipe 4 and end pieces 5.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above and below, and of corresponding application German P 41 27 988.3, filed Aug. 23, 1991, are hereby incorporated by reference.

EXAMPLES

In tests, dimethylformamide (DMF) was used as the absorption agent.

At a pressure of about 10 bars in the absorption column, a resaturation of the DMF up to about 10 to 40% of complete saturated was obtained as a function of the ethylene/ethane ratio on the respective tray of the absorption column, and at 30 bars, a resaturation of the DMF up to about 15 to 42% was obtained without foam formation occurring at either pressure level and at even at the highest degree of resaturation.

The total number of plates in the absorption column is approximately between 20 and 50, and, for example, an substantially acetylene-free liquid $C_2$ stream can be introduced into an absorption column having 42 plates, at the fifth, tenth, fifteenth and twentieth plate. (The number of plates is counted from the bottom of the absorption column toward the top.)

DETAILED EXAMPLE

A crude gas stream with a temperature of 225.0° K and a pressure of 10.0 bars containing

| 1.0 vol. % | $C_2H_2$ |
| 84.0 vol. % | $C_2H_4$ |
| 14.0 vol. % | $C_2H_6$ and |
| 1.0 vol. % | $C_{3+}$ | is fed into the absorption column. According to the above described process, a substantially acetylene-free liquid $C_2$ stream is introduced in the absorption column. This substantially acetylene-free $C_2$ stream can be obtained from the $C_2$ reflux stream of product. In this case the substantially acetylene-free $C_2$ stream has the same composition as the overhead $C_2$ product stream:

| $C_2H_2$ | <1 ppm |
| $C_2H_4$ | 85.7 vol. % |
| $C_2H_6$ | 14.3 vol. % |

Alternatively, an external liquid acetylene-free $C_2$ stream can be used as the substantially acetylene-free $C_2$ stream. Such an external substantially acetylene-free $C_2$ stream can be, for example, pure ethylene, e.g., from a $C_2$ cycle of the petrochemical plant, an external substantially acetylene-free $C_2$ stream must be used, if no reflux stream is returned to the top of the absorption column.

This invention is also suitable for the absorption for all acetylenes from hydrocarbon streams, for example, for the removal of methyl acetylene from a $C_3$ stream.

It is also contemplated that this invention will be useful in any gas absorption column, in order to prevent foaming.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for removing acetylene from a crude gas mixture containing mostly $C_2$ hydrocarbons by scrubbing with an absorption agent in a plate absorption column having a head and a bottom wherein the crude gas mixture is fed into a lower zone of the absorption column; fresh or regenerated absorption agent is fed into an upper zone of the absorption column, loaded absorption agent is withdrawn from the bottom of the absorption column and is fed to a regeneration stage, a substantially acetylene-free product gas stream is withdrawn from the head of the absorption column and substantially acetylene-free liquid $C_2$ stream is introduced into the absorption column at a location between the feed point for the crude gas mixture and the feed point for absorption agent, the improvement which comprises introducing said substantially acetylene-free liquid $C_2$ stream as finely distributed droplets into a mixing zone in the column, said mixing zone containing accumulated absorption agent.

2. A process according to claim 1, wherein said mixing zone is incorporated in a plate in the absorption column, and wherein absorption agent falling from an upper plate and said substantially acetylene-free liquid $C_2$ stream from outside the absorption column are introduced into said mixing zone.

3. A process according to claim 2, wherein the absorption agent is introduced by an immersion tube in the mixing zone.

4. A process according to claim 2, wherein the introduction of the substantially acetylene-free liquid $C_2$ stream into the mixing zone takes place at a location below the introduction of the absorption agent into the mixing zone.

5. A process according to claim 2, wherein the substantially acetylene-free liquid $C_2$ stream has a temperature below the temperature of the absorption agent entering the mixing zone.

6. A process according to claim 1, wherein the substantially acetylene-free liquid $C_2$ stream is introduced into the lower two-thirds of the absorption column.

7. A process according to claim 1, wherein the substantially acetylene-free liquid $C_2$ stream is introduced into the lower half of the absorption column.

8. A process according to claim 1, wherein the substantially acetylene-free liquid $C_2$ stream is fed as a plurality of streams into several plates in the absorption column.

9. A process according to claim 1, wherein the mixing zone is filled with packing.

10. A process according to claim 1, further comprising condensing the substantially acetylene-free product gas stream from the head of the absorption column and recycling a part of the resultant condensate as said substantially acetylene-free liquid $C_2$ stream as finely distributed droplets into said mixing zone.

11. A process according to claim 5, wherein the substantially acetylene-free liquid $C_2$ stream has a temperature of 2°–15° below the temperature of the absorption agent.

* * * * *